United States Patent [19]

Moran et al.

[11] 4,374,249

[45] Feb. 15, 1983

[54] [4R]-3-(ω-AROYLPROPIONYL)-4-THIAZOLIDINECARBOXYLIC ACIDS AND ESTERS

[75] Inventors: Daniel B. Moran, Suffern; Jay D. Albright, Nanuet, both of N.Y.

[73] Assignee: American Cyanamid Company, Stamford, Conn.

[21] Appl. No.: 219,766

[22] Filed: Dec. 23, 1980

[51] Int. Cl.$^3$ .................................................. C07D 277/04
[52] U.S. Cl. .................................... 548/201; 424/270
[58] Field of Search ................. 548/201, 200; 424/270

[56] References Cited

U.S. PATENT DOCUMENTS 4,282,235  8/1981  Ondetti ................................ 548/200

FOREIGN PATENT DOCUMENTS 608925  9/1948  United Kingdom .

Primary Examiner—Nicholas S. Rizzo
Attorney, Agent, or Firm—Edward A. Conroy, Jr.

[57] ABSTRACT

This disclosure describes novel [4R]-3-(ω-aroylpropionyl)-4-thiazolidinecarboxylic acids and esters and the cationic salts thereof which are useful as hypotensive agents in mammals.

20 Claims, No Drawings

[4R]-3-(ω-AROYLPROPIONYL)-4-THIAZOLIDINECARBOXYLIC ACIDS AND ESTERS

PRIOR ART

U.S. Pat. No. 4,192,878 (Squibb)

BRIEF SUMMARY OF THE INVENTION

This invention relates to new organic compounds and, more particularly, is concerned with novel substituted [4R]-3-(ω-aroylpropionyl)-4-thiazolidinecarboxylic acids and esters thereof which may be represented by the following general formula:

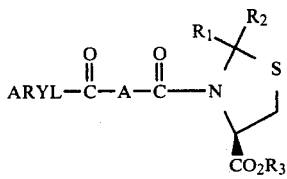

wherein A is

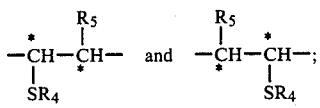

$R_1$ and $R_2$ are selected from the group consisting of hydrogen, lower alkyl ($C_1$–$C_3$), phenyl and mono substituted phenyl, wherein the substituents are chloro, fluoro, trifluoromethyl, lower alkyl ($C_1$–$C_4$), and methoxy, with the proviso that when $R_1$ is phenyl or substituted phenyl, $R_2$ must be hydrogen; $R_3$ is hydrogen, or lower alkyl having from 1–4 carbon atoms; $R_4$ is selected from the group comprising hydrogen, benzoyl and lower alkanoyl ($C_1$–$C_4$); $R_5$ is hydrogen and lower alkyl having from 1–3 carbon atoms; ARYL is selected from the group consisting of 1-naphthyl, 2-naphthyl, 4-chloro-1-naphthyl, 4-methoxy-1-naphthyl, 5,6,7,8-tetrahydro-1-naphthyl, 5,6,7,8-tetrahydro-2-naphthyl, 4-biphenylyl, 5-indanyl, 4-indanyl and moieties of the formula:

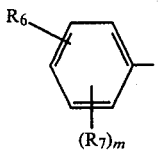

wherein $R_6$ is selected from the group consisting of hydrogen, fluoro, chloro, bromo, trifluoromethyl, cyano, phenoxy, halophenoxy, phenylthio, halophenylthio, alkyl having from 1–4 carbon atoms and alkoxy having from 1–4 carbon atoms; $R_7$ is selected from the group consisting of chloro, fluoro, bromo, alkyl having from 1–4 carbon atoms and alkoxy having from 1–4 carbon atoms; where m is zero, one or two.

Suitable alkyl and alkoxy groups contemplated by the present invention are, for example, methyl, ethyl, n-propyl, isobutyl, methoxy, ethoxy, isopropoxy, sec-butoxy, etc.; and the pharmacologically acceptable cationic salts thereof.

The novel compounds of the present invention possess asymmetric carbon atoms (which are indicated by asterisks) and thus exist in diastereoisomeric forms.

DETAILED DESCRIPTION OF THE INVENTION

The novel substituted [4R]-3-(ω-aroylpropionyl) -4-thiazolidinecarboxylic acids and esters thereof of the present invention are generally obtainable as white to yellow crystalline materials having characteristic melting points and absorption spectra or are obtained as white or yellow glasses with characteristic absorption spectra. They are generally soluble in many organic solvents such as lower alkanols, tetrahydrofuran, dioxane, chloroform, and the like.

Also included within the purview of the present invention are the cationic salts of the compounds of the above general formulae wherein $R_3$ is hydrogen. The useful pharmaceutically acceptable salts of the compounds wherein $R_3$ is hydrogen are those with pharmacologically acceptable metal cations, ammonium, amine cations, or quaternary ammonium cations. Preferred metal cations are those derived from the alkali metals, e.g., lithium, sodium and potassium, and from the alkaline earth metals, e.g., magnesium and calcium, although cationic forms of other metals, e.g., aluminum, copper, iron and in particular zinc, are within the scope of the invention. Pharmacologically acceptable amine cations are those derived from primary, secondary or tertiary amines such as mono-, di- or trimethylamine, ethylamine, dibutylamine, triisopropylamine, N-methylhexylamine, decylamine, allylamine, cyclopentylamine, dicyclohexylamine, mono- or dibenzylamine, α- or β-phenylethylamine, ethylenediamine, and arylaliphatic amines containing up to and including 18 carbon atoms, as well as heterocyclic amines, e.g. piperidine, morpholine, pyrrolidine, piperazine and lower alkyl derivatives thereof, e.g. 1-methylpiperidine, 4-ethylmorpholine, 1-isopropylpyrrolidine, 1,4-dimethylpiperazine, and the like, as well as amines containing water-solubilizing or hydrophilic groups, e.g. mono-, di- or triethanolamine, N-butylethanolamine, 2-amino-1-butanol, 2-amino-2-ethyl-1,3-propanediol, tris(hydroxymethyl) aminomethane, N-phenylethanolamine, galactamine, N-methylglucosamine, ephedrine, phenylephrine, epinephrine, procaine, and the like. Examples of suitable pharmacologically acceptable quaternary ammonium cations are tetramethylammonium, tetraethylammonium, benzyltrimethylammonium, phenyltriethylammonium, and the like.

Angiotensin II is a powerful vasoconstrictor agent that has been implicated as the main causative agent in the etiology of renovascular hypertension. Angiotensin II is formed from angiotensin I by the action of angiotensin converting enzyme. Angiotensin I is a biologically inert decapeptide cleaved from the blood protein angiotensinogen by the action of the enzyme renin [Oparil et al., New England J. of Med., 291, 389–457 (1974)]. Angiotensinogen and renin are also biologically inert. Agents that inhibit angiotensin converting enzyme can therefore counteract the pressor effect of angiotensin I since this is due only to its conversion to angiotensin II. These agents can be used therapeutically in the treatment of forms of renovascular and malignant hypertension as well as other forms of angiotensin dependent hypertension [Gavras, et al., New England J. of Med., 291, 817 (1974)].

The novel compounds of this invention inhibit angiotensin converting enzyme and thus inhibit the conversion of angiotensin I to angiotensin II and are, therefore, useful in reducing hypertension, especially angiotensin related hypertension in various mammalian species. The activity of the novel compounds of this invention as hypotensive agents was established in two systems which measure their ability as angiotensin converting enzyme inhibitors; by utilizing a spectrophotometric assay of the compounds in vitro and by the measurement of the blood pressure lowering effect of the compounds in the aorta-coarcted renal hypertensive rats.

Spectrophotometric Assay for Angiotensin Converting Enzyme Inhibitors

The in vitro activity for inhibition of the angiotensin converting enzyme (ACE) was measured by the method of Cushman, D. W. and Cheung, H. S., Biochem. Pharmacol., 20, 1637–1648 (1971), using benzoylglycyl-histidyl-leucine as the substrate. The reaction mixture consisted of 50 μl. of potassium phosphate (500 mM., pH 10.2), 30 μl. of sodium chloride (2500 mM.), 25 μl. of substrate (50 mM.), 30 to 50 μl. of the crude extract of ACE, 10 μl. of test compound (2.5 mM.) or vehicle and a suitable amount of distilled water to give a total volume of 250 μl. This reaction mixture was incubated for 30 minutes at 37° C. and the reaction was then terminated by the addition of 250 μl. of 1 N hydrochloric acid. The hippuric acid was then extracted with 1.5 ml. of ethyl acetate by vortex mixing for 15 seconds. After centrifugation, one ml. of the ethyl acetate layer was pipetted into a new tube and evaporated to dryness. The extracted hippuric acid was then dissolved in one ml. of water and the amount of this acid was then measured by its absorbance at 228 nm. The ACE was extracted from rabbit lung acetane powder (Pel-Freez, Biol. Inc.) by blending 5 g. of the powder in 50 ml. of phosphate buffer (50 mM., pH 8.3) and then centrifuging at 40,000 g for 40 minutes. The supernatant was then kept at 5° C. and used as the enzyme source. The activity of the ACE inhibitor was calculated as the percent inhibition of ACE activity compared to the control value of that particular assay. A full dose-response inhibitory curve is then performed to determine the $IC_{50}$ value which may be defined as the molar concentration of a compound that will inhibit ACE activity by 50%.

Representative compounds of the present invention and their corresponding $IC_{50}$ values as determined by the above described procedure are set forth in Table I.

TABLE I

| Angiotensin Converting Enzyme Inhibitors | |
|---|---|
| Compound | $IC_{50}$ ($10^{-7}$ M) |
| [4R]-3-[3-Acetylthio-3-(4-fluorobenzoyl)-propionyl]-4-thiazolidinecarboxylic acid, 2,4,6-trimethylbenzyl ester | 168 |
| [4R]-3-(2-Acetylthio-3-benzoylpropionyl)-4-thiazolidinecarboxylic acid | 84 |
| [4R-(4R*,2'S*)]-3-(3-Acetylthio-3-benzoyl-2-methylpropionyl)-4-thiazolidinecarboxylic acid | 0.67 |

Measurement of Arterial Blood Pressure in Aorta-Coarcted Renal Hypertensive Rats Male, Sprague-Dawley normotensive rats, weighing 300–325 g. (Charles River Breeding Lab. Inc., Wilmington, Mass.) were maintained on Purina Laboratory Chow and tap water ad libitum for 1–7 days before use. Hypertension was induced by complete ligation of the aorta between the origin of the renal arteries, according to the method of Rojo-Ortega, J. M. and Genest, J., A Method for Production of Experimental Hypertension in Rats, in Can. J. Physiol. Pharmacol., 46, 883–885 (1968), with modifications of the surgical procedures. Thus, rats were anesthetized with methohexital sodium at 66 mg./kg. of body weight, intraperitoneally and were laid on their right side. An incision was made just below the rib cage on their left side. With a cotton-tip swab, the fat was gently pushed back to expose the left kidney. The kidney was held gently between the thumb and the forefinger outside of the body cavity. The aorta was completely ligated between the origin of the renal arteries with a No. −000 silk suture. Care was taken to avoid the occlusion of the mesenteric artery. The wound was then closed in two layers using a 4–0 polyglycolic acid suture on the muscle and wound clips on the skin. The wound is then sprayed with No. 3 thimerosal aerosol. Following this surgery, the rats were returned to their cages and provided with Purina Laboratory Chow and water ad libitum. Six days after the surgery, the conscious rats were restrained on rat boards with elastic tape. The neck area was locally anesthetized by subcutaneous infiltration of 2% lidocaine. After the trachea was cannulated and the rat respired spontaneously, the carotid artery was isolated and cannulated with a nylon cathether (inside diameter 0.015", outside diameter 0.030") which was connected to a Statham P23Gb pressure transducer—Gould Brush recorder (Model 2400) for monitoring blood pressure. The test compounds were dissolved in a small amount of ethanol and then diluted to the desired concentration with saline. Both the solution of the test compound and the vehicle alone are administered orally and run parallel in each experiment.

The novel compounds of the present invention have thus been found to be highly useful for lowering elevated blood pressure in mammals when administered in amounts ranging from about one mg. to about 1000 mg. per kilogram of body weight per day. A preferred dosage regimen for optimum results would be from about 10 mg. to about 300 mg. per kilogram of body weight per day. The dosage regimen may be adjusted to provide the optimum therapeutic response. For example, several divided doses may be administered daily or the dose may be proportionally reduced as indicated by the exigencies of the therapeutic situation. The active compounds are preferably administered orally but may be administered in any convenient manner such as by the intravenous, intramuscular or subcutaneous routes.

Compositions according to the present invention having the desired clarity, stability and adaptability for parenteral use are obtained by dissolving or suspending the active compound in a vehicle consisting of a polyhydric aliphatic alcohol or mixtures thereof. Especially satisfactory are glycerin, propylene glycol and polyethylene glycols. The polyethylene glycols consist of a mixture of non-volatile, normally liquid polyethylene glycols which are soluble in both water and organic liquids and which have molecular weights of from about 200 to 1500. Although the amount of active compound dissolved or suspended in the above vehicle may vary, the amount of active substance in the composition is such that dosage in the range of about 10 to 500 mg. of compound is obtained. Although various mixtures of the aforementioned non-volatile polyethylene glycols may be employed, it is preferred to use a mixture having an average molecular weight of from about 200 to about 400.

In addition to the active compound, the parenteral solutions or suspensions may also contain various preservatives which may be used to prevent bacterial and fungal contamination. The preservatives which may be used for these purposes are, for example, myristyl-gamma-picolinium chloride, benzalkonium chloride, phenethyl alcohol, p-chlorophenyl-α-glycerol ether, methyl and propyl parabens and thimerosal. As a practical matter, it is also convenient to employ antioxidants, such as, for example, sodium bisulfite, sodium metabisulfite and sodium formaldehyde sulfoxylate. Generally, from about 0.05 to about 0.2% concentrations of antioxidant are employed.

The active compounds of the present invention may be orally administered, for example, with a inert diluent or with an assimilable edible carrier, or they may be enclosed in hard or soft shell gelatin capsules, or they may be compressed into tablets, or they may be incorporated directly with the food of the diet. For oral therapeutic administration, the active compounds may be incorporated with excipients and used in the form of tablets, troches, capsules, suspensions, syrups, wafers and the like. Such compositions and preparations should contain at least 0.1% active compound. The percentage of the compositions and preparations may, of course, be varied and may conveniently be between about 2% to about 60% of the weight of the unit. The amount of active compound in such therapeutically useful compositions is such that a suitable dosage will be obtained.

The tablets, troches, pills, capsules and the like may also contain the following: A binder such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose or lactose may be added or a flavoring agent such as peppermint, oil of wintergreen, or cherry flavoring. When the dosage unit form is a capsule, it may contain, in addition to materials of the above type, a liquid carrier such as a fatty oil. Various other materials may be present as coatings or to otherwise modify the physical form of the dosage unit. For instance, tablets, pills or capsules may be coated with shellac, sugar or both. A syrup or suspension may contain the active compound, sucrose as a sweetening agent, methyl and propyl parabens as preservatives, a dye and flavoring such as cherry or orange flavor. Of course, any material used in preparing any dosage unit form should be pharmaceutically pure and substantially non-toxic in the amounts employed.

The novel compounds of formula I, wherein A is

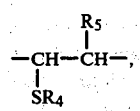

of the present invention may be prepared in accordance with the following reaction scheme:

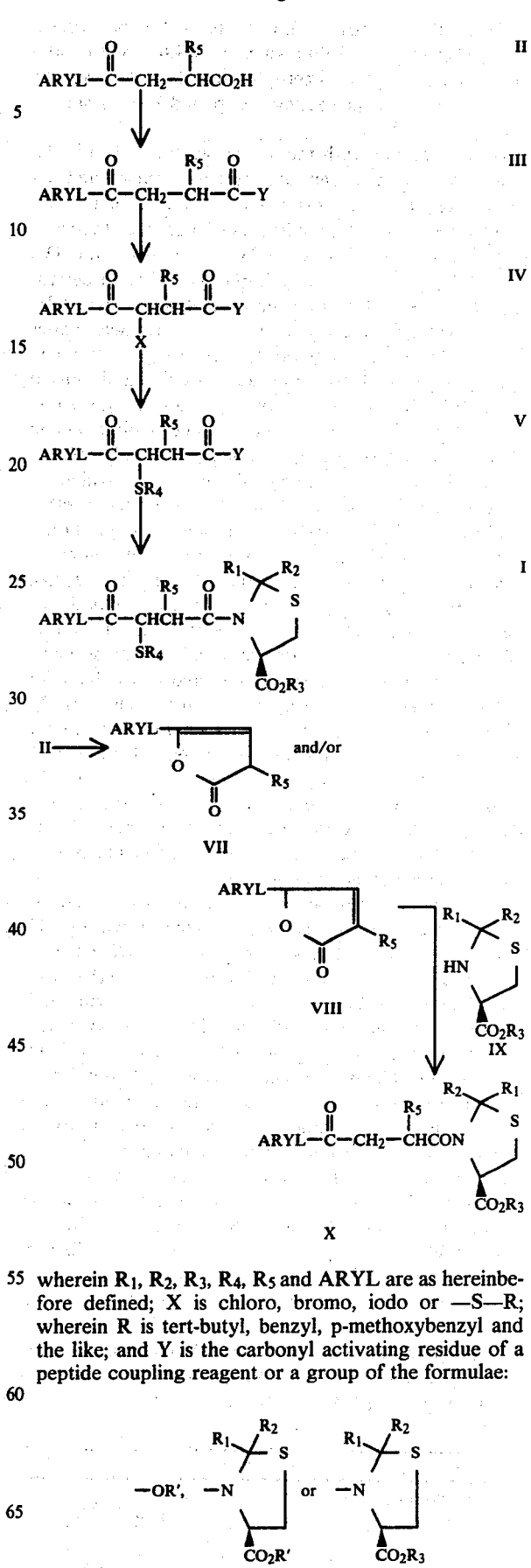

wherein $R_1$, $R_2$, $R_3$, $R_4$, $R_5$ and ARYL are as hereinbefore defined; X is chloro, bromo, iodo or —S—R; wherein R is tert-butyl, benzyl, p-methoxybenzyl and the like; and Y is the carbonyl activating residue of a peptide coupling reagent or a group of the formulae:

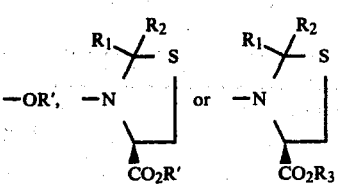

wherein R' is hydrogen, alkyl having 1-4 carbon atoms, phenyl, p-tolyl, p-methoxybenzyl, 2,4,6-trimethylbenzyl, trimethylsilyl, 2-trimethylsilylethyl and the like or a suitable carbonyl protecting group; and $R_3$ is as hereinbefore defined.

In accordance with the above reaction scheme, the carboxyl group of an appropriately substituted ω-aroylalkanoic acid (II) is converted to a carbonyl activated derivative (III) or in accordance with the reaction scheme, derivatives (IV) (Y=OH) and (V) (Y=OH) are converted to carbonyl activated derivatives. The carbonyl activated derivatives of (III), (IV) and (V) are prepared by reaction of the free acids under standard reaction conditions for activating the carboxyl groups of N-protected amino acids. For example, mixed anhydrides are prepared in situ by treatment of the free acids with bases such as trialkylamines (triethylamino and the like), N-methylmorpholine, pyridine, N-methylpiperidine and the like to give the amine salts which are reacted with lower alkyl chloroformates such as ethyl chloroformate, t-butyl chloroformate, isobutyl chloroformate, benzyl chloroformate, trityl chloroformate and the like. Alternatively, the free acids are reacted with N,N'-carbonyldiimidazole or related peptide coupling reagents such as N,N'-carbonyl-1,2,4-triazole to form activated carbonyl derivatives. Derivatives where Y is O-hydroxysuccinimide or O-hydroxyphthalimide are prepared by reaction of the free acids with N-hydroxysuccinimide or N-hydroxyphthalimide in the presence of a carbodiimide such as N,N-dicyclohexylcarbodiimide. Derivatives wherein Y is a residue of a peptide coupling reagent or an activated ester are reacted with L-thiazolidine-4-carboxylic acid or L-thiazolidine-4-carboxylic acid derivatives under conventional coupling conditions.

The amides are obtained by reacting an acid halide of (II) or preferably a carbonyl activated derivative (III) with an L-thiazolidine-4-carboxylic acid (IX) ($R_3$=H) or an ester of L-thiazolidine-4-carboxylic acid (IX) such as an alkyl ($C_1$-$C_4$) ester, benzyl ester, 2,4,6-trimethylbenzyl ester and other L-thiazolidine-4-carboxylic acid derivatives (IX) with a protected acid function which is removed in a later step. The reaction conditions for the formation of the carboxyl activated derivatives and conditions for coupling to L-thiazolidine-4-carboxylic acid derivatives, such as time, temperature, solvents, etc., are well known in the art. In general, the reactions are carried out at 0° C. to 50° C. in solvents such as tetrahydrofuran, dioxane, N,N-dimethylformamide, dimethylsulfoxide, toluene, acetonitrile and the like for 1-24 hours.

Further elucidation of the meaning of the terms employed herein is afforded by the following table wherein typical peptide coupling reagents are listed in the left column and the corresponding carbonyl activating residues are listed in the right column:

| Reagent | —Y |
|---|---|
| N—hydroxyphthalimide | 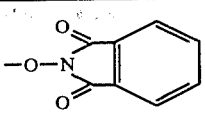 |
| dicyclohexylcarbodiimide | |
| N,N'—carbonyldiimidazole | |
| benzyl chloroformate | |
| N—hydroxysuccinimide | |
| activated ester | —S—Aryl |
| mixed anhydride | —O—C(=O)—C(CH₃)₃<br>—O—C(=O)—O—Alkyl<br>—SO₂—Aryl |

Numerous other peptide coupling reagents are available and well known to the art such as unsaturated ethers, α-chlorovinyl ethyl ether, ethoxyacetylene, ketenimines and ketenes, ynamines, acyloxyphosphonium ions EEDQ, silicon tetrachloride, 1,2-oxazolium salts, and the like. These all provide a carbonyl activating residue (—Y) and may be readily used for the conversion of (VI) to (V) when Y is to be a "carbonyl activating residue of a peptide coupling reagent." The reaction conditions for such conversions are well known in the art and may be readily found in such literature references as SYNTHESIS, September 1972, pages 453-463 by Klausner and Bodansky.

Alternatively, 3-(aroyl)propionic acids (II) may be cyclized to 5-aryl-2(3H)-furanones (VII) or 5-aryl-2(5H)-furanones (VIII) which react with L-thiazolidine-4-carboxylic acid derivatives (IX) to give the intermediates (X). The cyclization of acids (II) may be carried out in lower alkanoic acid anhydrides or in inert solvents such as benzene, toluene, xylene and the like in the presence of one to three moles of a lower alkanoic acid anhydride. Coupling of furanones (VII) or (VIII) with L-thiazolidine-4-carboxylic acid derivatives (IX) may be carried out in the presence of one mole of trialkylamine such as trimethylamine, triethylamine and the like in solvents such as acetonitrile, dioxane and the like for 10-48 hours to give derivatives (X).

The conversion of the intermediates (III) to the corresponding 3-(X-substituted)propionic acid derivative (IV) wherein X consists of the hereinabove defined leaving groups is readily achieved by conventional methods well known in the art. For example, the chloro, bromo and iodo derivatives may be prepared by treating a compound of formula (III) or (X) with a halogenating agent such as chlorine, bromine, N- iodosuccinimide, and the like in a solvent such as chloroform, carbon tetrachloride, acetic acid or dioxane at 25°-75° C. for 12-24 hours. Those compounds wherein X is —S—R may be obtained from the halo derivatives by treatment with an alkali metal mercaptide under standard conditions.

As desired, the ω-aroylalkanoic acids (II) may be coupled to an L-thiazolidine-4-carboxylic acid derivative

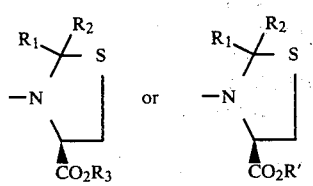

to give intermediates (III) which are then converted to products (I) through intermediates (IV) and (V). Alternatively, intermediates (III) wherein Y is a carboxyl protecting group may be converted to intermediates (IV) or (V) at which point the protecting group may be removed and the intermediates (IV) or (V), (Y=OH), coupled to L-thiazolidine-4-carboxylic acid or L-thiazolidine-4-carboxylic acid derivatives.

The ω-aroylalkanoic acids (II), wherein $R_5$ is other than hydrogen, have one asymmetric carbon atom and the D and L isomers may be prepared by resolution of the racemic mixture. Activation of the carboxyl group of the resolved isomers then gives compounds of structure (III) wherein the carbon atom bearing the $R_5$ group has either the D or the L configuration. Conversion of the resolved compounds of structure (III) to the reactive intermediates (IV) gives compounds which are diastereoisomers. Each diastereoisomer may then be converted to compounds of structure (V) as shown in the reaction scheme. Alternatively, racemic compounds of structure (II) wherein $R_5$ is lower alkyl may be coupled to L-thiazolidine-4-carboxylic acid derivatives to give compounds of structure (III) which exist as diastereoisomeric forms and may be separated by conventional means. For example, the diastereoisomeric forms of [4R]-3-(3-benzoyl-2-methylpropionyl)-4-thiazolidinecarboxylic acid may be separated by preferential crystallization of one diastereoisomer and isolation of the other diastereoisomer from the mother liquors. In this manner diastereoisomeric forms of structural type (IV) may be prepared and converted to the compounds of structure (I) which are inhibitors of the angiotension converting enzyme. The reactive intermediates (IV) are reacted with the anion of a thioacid of formula

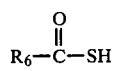

wherein $R_6$ is phenyl or alkyl having up to 3 carbon atoms. Suitable anions of thioacids and thiolating reagents useful in the displacement reaction are those from alkali metals ($K^+$, $Na^+$), alkaline earth metals such as calcium and magnesium, and organic bases such as ammonia, trialkylamines, and the like. Removal of the acyl group by reaction with hydroxylamine, ammonium hydroxide or dilute inorganic bases gives the compounds of structure (I) wherein $R_4$ is hydrogen. Under appropriate conditions intermediates (IV) and (V) wherein X is —S—R and Y is

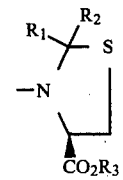

may be converted directly to products (I) wherein $R_4$ is hydrogen by removal of a thio protecting group. For example, derivatives wherein R is a thio protecting group such as t-butyl, p-methoxybenzyl, $C_6H_5CH_2O_2CS$— and the like may be deblocked under acidic conditions [HBr-HOAc, $CF_3CO_2H$, $(CF_3CO_2)_2Hg$ and the like] known to the art.

Derivatives (V) wherein Y is

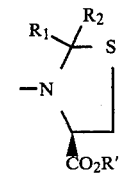

and $R_4$ is as previously defined, and R' is a carboxyl protecting group, may be converted to products (I) ($R_3$=H) by removal of the carboxyl protecting group under conventional conditions. In general, carboxyl protecting groups which are removed under acidic conditions are preferred. For example, 2,4,6-trimethylbenzylesters are cleaved by treatment with anhydrous hydrogen bromide in acetic acid at 0°-50° C. for 1-24 hours. Trimethylsilyl and 2-trimethylsilylethyl are removed under conventional conditions known to the art. The reactions illustrated in the reaction scheme may be carried out with esters ($R_3$=lower alkyl) to give the products (I) wherein $R_3$ is lower alkyl. In the products (I) (wherein $R_3$ is 2,4,6-trimethylbenzyl) the ester group may be removed with anhydrous hydrogen bromide in acetic acid to give the free acid derivatives of (I). The novel compounds of formula (I)

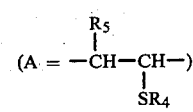

may be prepared in accordance with the following reaction scheme:

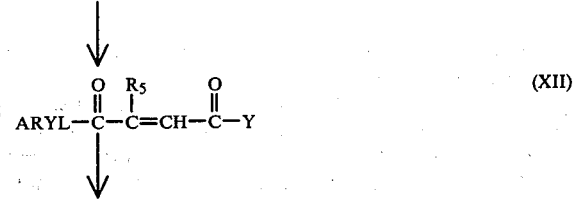

-continued

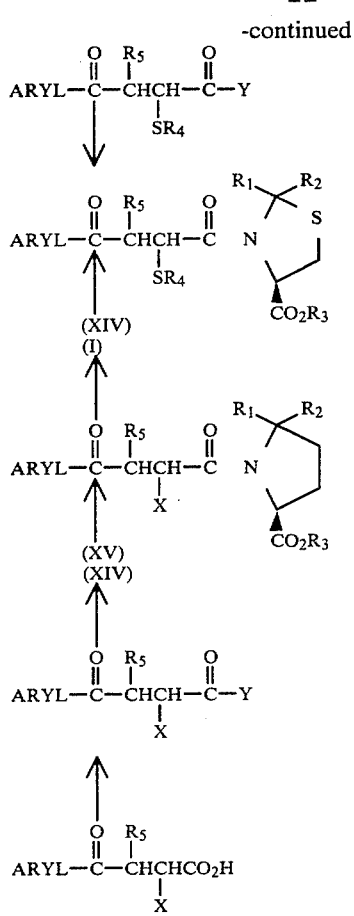

wherein R₁, R₂, R₃, R₄, R₅, ARYL, X and Y are as hereinbefore defined. In accordance with the above reaction scheme, an appropriately substituted 3-(aroyl)acrylic acid (XI) or 3-(X-substituted)propionic acid (XVI) is converted to a carbonyl activated derivative (XII) or (XV). The reaction conditions for the formation of such carbonyl activated derivatives such as time, temperature, solvents, etc. are well known in the art and are hereinbefore discussed. The carboxyl activated derivatives (XII), (XIII) and (XV) are prepared by treatment of the free acid (XI) and (XVI) with peptide coupling reagents as hereinbefore discussed (see table for carbonyl activating residues).

Derivatives (XII), (XIII) or (XV) wherein Y is a residue of a peptide coupling reagent or an activated ester are reacted with an L-thiazolidine-4-carboxylic acid or an L-thiazolidine-4-carboxylic acid derivative of the formulae:

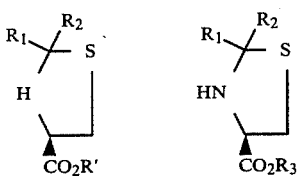

wherein R' and R₃ are as previously defined to give intermediates (XII) and (XV).

The intermediates (XII) and (XV) are reacted with a thiolating reagent which gives the products (I) directly or intermediates (V) or (XIV) convertible into products (I). Thiolating reagents add 1, 4 to the ketone carbonyl of intermediates (XI) and (XII). Suitable thiolating reagents are H₂S, H—S—C(CH₃)₃ and HSR₄. Preferred reagents are hydrogen sulfide or a thiolating agents of the formula:

wherein R₆ is phenyl or alkyl having up to 3 carbon atoms. Preferred conditions for the addition of a thiolating reagent are reaction in inert solvents such as chloroform, dichloromethane, carbon tetrachloride, dimethylformamide, tetrahydrofuran, dioxane, acetonitrile, toluene, lower alkanols and the like at 0°–10° C. for one to 24 hours.

The intermediates (XVI), (XV) and (XIV) are reacted with the anion of a thiolating reagent. Suitable thiolating reagents are Na₂S, NaHS and anions of a thiolating reagents of the formulae HSC(CH₃)₃ and

wherein R₆ is as previously defined.

Conversion of compounds (XIII) and (XV) wherein Y is a group of the formula:

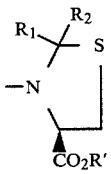

and R' is a carboxyl protecting group as previously defined is carried out by removal of the protecting group to give products (I) wherein R₃=H. Carboxyl protecting groups which are removed under acidic conditions are preferred. The reactions illustrated in the reaction scheme may be carried out with esters of [4R]-thiazolidine-4-carboxylic acid derivatives (R₃=lower alkyl) to give products (I) wherein R₃ is lower alkyl. Derivatives which contain a thio protecting group may be converted to products (I) wherein R₄ is hydrogen by removing the protecting group under conventional conditions.

The invention will be described in greater detail in conjunction with the following specific examples.

EXAMPLE 1

[4R-(4R*,2'S*)]-3-(3-Acetylthio-3-benzoyl-2-methylpropionyl)-4-thiazolidinecarboxylic acid A mixture of 100 g. of 3-benzoyl-2-methylpropionic acid and 500 ml. of acetic anhydride is heated on a steam bath for 4 hours. The mixture is concentrated under vacuum. To the residue is added toluene and the solvent removed under vacuum (three times) to give 91 g. of 3-methyl-5-phenyl-2(3H)furanone.

The preceding compound (90.6 g.; 0.52 mole) in 100 ml. of isopropanol is added to a mixture of 69.2 g. (0.52 mole) of L-thiazolidine-4-carboxylic acid and triethylamine (52.6 g; 0.52 mole) in 500 ml. of isopropanol which had been refluxed for 3 hours. The mixture is refluxed for 24 hours and the solvent removed in vacuo.

The residue is partitioned between water and dichloromethane and the organic layer separated and dried over sodium sulfate. The aqueous phase is added dropwise to dilute aqueous hydrochloric acid and then extracted with ethyl acetate. The organic layer is dried over sodium sulfate and concentrated to give 8.0 g. of crystals, m.p. 175°–180° C. Recrywtallization from acetone-hexane gives 6.5 g. of [4R-(4R*,2'R*)]-3-(3-benzoyl-2-methylpropionyl)-4-thiazolidinecarboxylic acid, as white crystals, m.p. 184°–186° C.; $[\alpha]_D^{23} -65° \pm 1$ (c, 0.818, $CH_3OH$).

The preceding compound (13.4 g.) is dissolved in 150 ml. of acetic acid and 7.0 g. of bromine is added. The mixture is stirred for 3 hours or until the bromine has reacted. The solvent is removed and the residue is partitioned between dichloromethane and water. The organic layer is dried over sodium sulfate and the solvent removed to give a tan glass. The tan glass (0.044 mole) is dissolved in 500 ml. of acetonitrile and added dropwise (¾ hour) to a stirred mixture of 10.0 g. (0.088 mole) of potassium thioacetate in 500 ml. of dichloromethane. The mixture is stirred at room temperature for 3 hours and 40 ml. of acetic acid added. The mixture is filtered and the filtrate is concentrated in vacuo to give a syrup. The syrup is partitioned between water and dichloromethane. The organic layer is separated, dried over sodium sulfate and concentrated in vacuo to give 15 g. of a viscous residue. The residue is chromatographed on a silica gel column with ethyl acetate:hexane (3:1) containing 1% acetic acid as eluent to give 8.3 g. of solid. The solid is chromatographed on a silica gel column with ethyl acetate:hexane (2:3) as eluent to give 6.0 g. of the product of the Examples as an off-white glass (one spot by thin layer chromatography on silica gel; solvent—ethyl acetate:hexane (3:1) containing 1% acetic acid).

EXAMPLE 2

[4R-(4R*,2'S*,3'R*)]-3-(3-Acetylthio-3-benzoyl-2-methylpropionyl)-4-thiazolidinecarboxylic acid A mixture of 25 g. (0.13 mole) of 3-benzoyl-2-methylpropionic acid and 15.5 ml. of acetic anhydride is refluxed for 4 hours. The solvent is removed in vacuo and the residue is stripped several times with toluene to give a mixture of 3-methyl-5-phenyl-2(3H)-furanone and 3-methyl-5-phenyl-2(5H)-furanone. The preceding mixture is dissolved is 200 ml. of dioxane and 17.3 g. (0.13 mole) of L-thiazolidine-4-carboxylic acid, and 13.2 g. (0.13 mole) of triethylamine is added. The mixture is refluxed for 38 hours and filtered while hot. The filtrate is concentrated in vacuo to provide a gum. The gum is partitioned between ethyl acetate and dilute aqueous hydrochloric acid. The organic layer is dried over sodium sulfate and the solvent is removed in vacuo. The residue is slurried in ether, filtered and the solid washed with n-hexane to give 6.0 g. of white crystals. Recrystallization from acetone-hexane with the aid of activated carbon gives 4.0 g. of [4R-(4R*,2'R*)]-3-(3-benzoyl-2-methylpropionyl)-4-thiazolidinecarboxylic acid. Bromination of the preceding compound gives a mixture of [4R-(4R*,2'S*,3'R*)]-3-(3-benzoyl-3-bromo-2-methylpropionyl)-4-thiazolidinecarboxylic acid and [4R-(4R*,2'S*,3'S*)]-3-(3-benzoyl-3-bromo-2-methylpropionyl)-4-thiazolidinecarboxylic acid. The mixture of diastereomers is reacted with potassium thioacetate in acetonitrile-dichloromethane and the product is chromatographed on silica gel as for Example 1 to give the product of the Example as a white powder.

EXAMPLE 3

Methyl
[4R-(4R*,2'S*)]-3-(3-acetylthio-3-benzoyl-2-methylpropionyl)-4-thiazolidinecarboxylate and Methyl
[4R-(4R*,2'R*)]-3-(3-acetylthio-3-benzoyl-2-methylpropionyl)-4-thiazolidinecarboxylate A 30.0 g. sample of L-thiazolidine-4-carboxylic acid is added to 300 ml. methanol saturated with anhydrous hydrogen chloride. The mixture is refluxed for one hour and the solvent is removed in vacuo. The residue is triturated with ether, filtered and the solid washed with ether and n-hexane to give 50.3 g. of methyl L-thiazolidine-4-carboxylate hydrochloride as white crystals. A 4.0 g. sample is recrystallized from methanol-ether to give 2.0 g. of white plates, m.p. 170° C. A 45.0 g. amount of the preceding compound is partitioned between water and ether and solid potassium carbonate is added. The ether layer is separated, dried over sodium sulfate and the solvent is removed. The residual oil is distilled in a bulb to bulb apparatus at 60° C. and 0.3 mm. to give 23.2 g. of methyl L-thiazolidine-4-carboxylate as an oil.

The preceding compound is reacted with 3-methyl-5-phenyl-2(3H)-furanone as for Example 1 to give methyl [4R-(4R*,2'R*)]-3-(3-benzoyl-2-methylpropionyl)-4-thiazolidinecarboxylate and methyl [4R-(4R*,2'S*)]-3-(3-benzoyl-2-methylpropionyl)-4-thiazolidinecarboxylate. Conversion of the preceding two diastereomers to the products of the Example is carried out as described for Example 1.

EXAMPLE 4

[4R-(4R*, 2'S*,3'R*)]-3-(3-Acetylthio-3-benzoyl-2-methylpropionyl)-4-thiazolidinecarboxylic acid and

[4R-(4R*,2'S*,3'S*)]-3-(3-Acetylthio-3-benzoyl-2-methylpropionyl)-4-thiazolidinecarboxylic acid To a solution of 79.9 g. of L-thiazolidine-4-carboxylic acid in 960 ml. of water containing 100.8 g. of sodium bicarbonate is added, dropwise over a 45 minute period, a solution of 100.8 g. of di-tert-butyldicarbonate in 960 ml. of dioxane. The mixture is stirred at room temperature for 16 hours. To the chilled mixture is added, dropwise, a solution of 120 ml. of concentrated hydrochloric acid in 600 ml. of water. The mixture is extracted with ethyl acetate and the extract is dried over sodium sulfate and the solvent is removed in vacuo. The residual oil is triturated with n-hexane to give 132 g. of [4R]-3,4-thiazolidinedicarboxylic acid, 3-tert-butyl ester as white crystals, m.p. 124°–127° C.

The preceding compound (132 g.; 0.57 mole) is dissolved in 400 ml. of N,N-dimethylformamide and 57.7 g. (0.57 mole) of triethylamine. To the solution is added, dropwise, a solution of 96.1 g. (0.57 mole) of 2,4,6-trimethylbenzylchloride in 200 ml. of N,N-dimethylformamide over a period of 20 minutes. The mixture is stirred at room temperature for 48 hours and is concentrated to one-half volume. The mixture is diluted with cold water and extracted with ethyl acetate. The extract is washed with dilute sodium bicarbonate solution, saturated sodium chloride solution and dried over sodium sulfate. The solvent is removed in vacuo and the residual oil is crystallized from n-hexane to give 148 g. of [4R]-3,4-thiazolidinedicarboxylic acid, 3-tert-butyl ester, 4-(2,4,6-trimethylbenzyl)ester as white crystals, m.p. 60°–62° C.

The preceding compound (148 g.; 0.40 mole) is added to a mixture of 95.11 g. (0.50 mole) of p-toluenesulfonic acid in 600 ml. of dry acetonitrile. The mixture is stirred at room temperature for 5.5 hours. An additional 19 g. (0.1 mole) of p-toluenesulfonic acid is added and the mixture is stirred at room temperature for 3 hours. The mixture is concentrated in vacuo and the residue is added to a mixture of ice and dichloromethane. The mixture is made basic by the addition of solid sodium carbonate. The organic layer is separated, washed with saturated sodium chloride solution and dried over sodium sulfate. The solvent is removed to give 123 g. of crystals. Recrystallization from ethyl acetate gives 64.0 g. of L-thiazolidine-4-carboxylic acid, 2,4,6-trimethylbenzyl ester as white crystals, m.p. 91°–93° C.

A mixture of the preceding compound (6.85 g.; 0.026 mole), 5.0 g. (0.026 mole) of 3-benzoyl-2-methylpropionic acid, 6.43 g. (0.026 mole) of ethyl 1,2-dihydro-2-ethoxy-1-quinolinecarboxylate and 200 ml. of dichloromethane is stirred at room temperature under argon for 18 hours. The mixture is washed with ice cold dilute hydrochloric acid, dried over sodium sulfate and the solvent removed in vacuo to give 16.0 g. of yellow oil. Chromatography over silica gel with ethyl acetate as solvent gives 11.0 g. of [4R]-3-(3-benzoyl-2-methylpropionyl)-4-thiazolidinecarboxylic acid, 2,4,6-trimethylbenzyl ester as a colorless oil.

A 4.5 g. amount of the preceding compound is dissolved in 100 ml. of acetic acid saturated with anhydrous hydrogen bromide and the mixture is stirred at room temperature for 18 hours. The mixture is concentrated in vacuo and the residue is partitioned between dilute sodium bicarbonate solution and ethyl acetate. The organic layer is removed. The aqueous layer is acidified with dilute hydrochloric acid and extracted with ethyl acetate. The extract is dried over sodium sulfate and the solvent is removed to give a white solid. Crystallization from acetone-hexane gives 0.5 g. of [4R-(4R*,2'R*)]-3-(3-benzoyl-2-methylpropionyl)-4-thiazolidinecarboxylic acid as white crystals, m.p. 185°–186° C.

As for Example 1, the preceding compound is converted to the (diastereomers) products of the Example.

EXAMPLE 5

[4R-(4R*,2'S*)]-3-[3-Acetylthio-3-(3-fluorobenzoyl)-2-methylpropionyl]-4-thiazolidinecarboxylic acid A 100 g. portion of 3-(3-fluorobenzoyl)-2-methylpropionic acid is heated with 500 ml. of acetic anhydride for 4 hours to give a mixture of 3-methyl-5-(3-fluorophenyl)-2(3H)-furanone and 3-methyl-5-(3-fluorophenyl)-2(5H)-furanone. The mixture, in isopropanol, is added to a mixture of L-thiazolidine-4-carboxylic acid and triethylamine in isopropanol. The reaction mixture is refluxed for 48 hours and the [4R-(4R*,2'R*]-3-[3-(3-fluorobenzoyl)-2-methylpropionyl]-4-thiazolidinecarboxylic acid is isolated. As for Example 1, the preceding compound is converted to the product of the Example which is isolated as an off-white solid.

EXAMPLE 6

[4R-(4R*,2'S*)]-3-[3-Acetylthio-3-(4-chlorobenzoyl)-2-methylpropionyl]-4-thiazolidinecarboxylic acid A 100 g. sample of 3-(4-chlorobenzoyl)-2-methylpropionic acid is heated with 500 ml. of acetic anhydride for 4 hours to give a mixture of 3-methyl-5-(4-chlorophenyl)-2(3H)-furanone and 3-methyl-5-(4-chlorophenyl)-2(5H)-furanone. The preceding mixture (0.10 mole), L-thiazolidine-4-carboxylic acid (0.10 mole) and triethylamine (0.10 mole) is dissolved in dioxane and the mixture is refluxed for 48 hours. The [4R-(4R*,2'R*]-3-[3-(4-chlorobenzoyl)-2-methylpropionyl]-4-thiazolidinecarboxylic acid is isolated by crystallization. The preceding compound is converted as for Example 1 to give the product of the Example as a white solid.

EXAMPLE 7

[4R-(4R*,2'S*)]-3-[3-Acetylthio-3-(4-fluorobenzoyl)-2-methylpropionyl]-4-thiazolidinecarboxylic acid Substituting 3-(4-fluorobenzoyl)-2-methylpropionic acid for 3-benzoyl-2-methylpropionic acid in the procedure of Example 1 gives the product of the Example.

EXAMPLE 8

[4R-(4R*,2'S*)]-3-[3-Acetylthio-3-(3-cyanobenzoyl)-2-methylpropionyl]-4-thiazolidinecarboxylic acid Substituting 3-(3-cyanobenzoyl)-2-methylpropionic acid for 3-benzoyl-2-methylpropionic acid in the procedure of Example 1 gives the product of the Example.

EXAMPLE 9

[4R-(R*,2'S*)]-3-[3-Acetylthio-3-(3-methoxybenzoyl)-2-methylpropionyl]-4-thiazolidinecarboxylic acid Substituting 3-(3-methoxybenzoyl)-2-methylpropionic acid for 3-benzoyl-2-methylpropionic acid in the procedure of Example 1 gives the product of the Example.

EXAMPLE 10

[4R-(4R*,2'S*)]-3-[3-Acetylthio-3-(4-tert-butylbenzoyl)-2-methylpropionyl]-4-thiazolidinecarboxylic acid Substituting 3-(4-tert-butylbenzoyl)-2-methylpropionic acid for 3-benzoyl-2-methylpropionic acid in the procedure of Example 1 gives the product of the Example.

EXAMPLE 11

[4R-(4R*,2'S*)]-3-[3-Acetylthio-3-(3,4-dichlorobenzoyl)-2-methylpropionyl]-4-thiazolidinecarboxylic acid Substituting 3-(3,4-dichlorobenzoyl)-2-methylpropionic acid for 3-benzoyl-2-methylpropionic acid in the procedure of Example 1 gives the product of the Example.

EXAMPLE 12

[4R-(4R*,2'S*)]-3-[3-Acetylthio-3-(3-trifluoromethylbenzoyl)-2-methylpropionyl]-4-thiazolidinecarboxylic acid Substituting 3-(3-trifluoromethylbenzoyl)-2-methylpropionic acid for 3-benzoyl-2-methylpropionic acid in the procedure of Example 1 gives the product of the Example.

EXAMPLE 13

[4R-(4R*,2'S*)]-3-(3-Benzoylthio-3-benzoyl-2-methyl-propionyl)-4-thiazolidinecarboxylic acid A mixture of 2.0 g. (0.015 mole) of L-thiazolidine-4-carboxylic acid and 2.72 g. (0.015 mole) of dicyclohexylamine is heated on a steam bath then 50 ml. of dry dioxane and 50 ml. of acetonitrile are added. To this mixture is added 4.2 g. (0.015 mole) of 3-benzoyl-2-methylpropionic acid, N-hydroxysuccinnimide ester, then the mixture is refluxed for 48 hours. The mixture is evaporated in vacuo. The residue is stirred with ethyl acetate and filtered. The filtrate is concentrated in vacuo and the residue is dissolved in dichloromethane. The dichloromethane is washed with sodium bisulfate and then extracted with saturated sodium bicarbonate solution. The sodium bicarbonate wash is added to dilute aqueous hydrochloric acid and the mixture is extracted with dichloromethane. The organic layer is dried over sodium sulfate and concentrated to an oil. The oil is crystallized from acetone-hexane to give [4R-(4R*,2'R*)]-3-(3-benzoyl-2-methylpropionyl)-4-thiazolidinecarboxylic acid as white crystals, m.p. 182°–183° C.; $[\alpha]_D^{23} -63° \pm 4$ (C, 0.24, $CH_3OH$).

The preceding compound is brominated with bromine in acetic acid to give a glass. The glass is reacted with sodium thiobenzoate to give the product of the Example as a glass.

EXAMPLE 14

[4R]-3-(3-Acetylthio-3-benzoyl-2-methylpropionyl)-2-(m-trifluoromethylphenyl)-4-thiazolidinecarboxylic acid To a solution of 10.0 g. (0.057 mole) of L-cysteine hydrochloride hydrate and 6.0 g. (0.061 mole) of potassium acetate in 280 ml. of ethanol:water (3:2) is added 13.06 g. (0.075 mole) of m-trifluoromethylbenzaldehyde dropwise over a 10 minute period. The mixture is stirred for 24 hours at room temperature and filtered. The solid (17.0 g.) is recrystallized from methanol to give 13.2 g. of [4R]-2-(m-trifluoromethylphenyl)-4-thiazolidinecarboxylic acid as white crystals, m.p. 152°–154° C.

Substituting the preceding compound for L-thiazolidine-4-carboxylic acid in the procedure of Example 1 gives the product of the Example.

EXAMPLE 15

Methyl [4R]-3-(3-acetylthio-3-benzoylpropionyl)-2-(m-trifluoromethylphenyl)-4-thiazolidinecarboxylate A mixture of 1.0 g. of [4R]-2-(m-trifluoromethylphenyl)-4-thiazolidinecarboxylic acid and 25 ml. of methanol saturated with anhydrous hydrogen chloride gas is heated on a steam bath for one hour. The solvent is removed in vacuo and the residue is partitioned between dichloromethane and saturated sodium bicarbonate solution. The organic layer is separated and concentrated to give 0.6 g. of methyl [4R]-2-(m-trifluoromethylphenyl)-4-thiazolidinecarboxylate as an oil.

A mixture of the preceding compound and 3-methyl-5-phenyl-2(3H)-furanone in dioxane is refluxed for 24 hours to give methyl [4R]-3-(3-benzoylpropionyl)-2-(m-trifluoromethylphenyl)-4-thiazolidinecarboxylate.

The preceding compound (0.001 mole) is reacted with (0.0011 mole) of bromine in acetic acid to give methyl [4R]-3-(3-bromo-3-benzoylpropionyl)-2-(m-trifluoromethylphenyl)-4-thiazolidinecarboxylate. The preceding compound is dissolved in dichloromethane:acetonitrile (1:1) and potassium thioacetate is added. The mixture is stirred at room temperature for 4 hours and worked up as for Example 1 to give the product of the Example.

EXAMPLE 16

Methyl [4R]-3-(3-acetylthio-3-benzoylpropionyl)-4-thiazolidinecarboxylate

A mixture of 0.735 g. (0.005 mole) of methyl L-thiazolidine-4-carboxylate, 1.29 g. (0.005 mole) of 3-(p-bromobenzoyl)propionic acid and 1.24 g. (0.005 mole) of ethyl 1,2-dihydro-2-ethoxy-1-quinolinecarboxylate in 50 ml. of dichloromethane is stirred at room temperature for 18 hours. The mixture is washed with dilute hydrochloric acid, dilute sodium bicarbonate solution and dried over sodium sulfate. The solvent is removed in vacuo to give 2.1 g. of methyl [4R]-3-(3-benzoylpropionyl)-4-thiazolidinecarboxylate.

The preceding compound is reacted with bromine in acetic acid and the resulting product is reacted with potassium thioacetate in dichloromethane-acetonitrile to give the product of the Example.

EXAMPLE 17

Methyl [4R]-3-[3-acetylthio-3-(4-fluorobenzoyl)propionyl]-4-thiazolidinecarboxylate A mixture of 3-(4-fluorobenzoyl)propionic acid (0.01 mole) and bromine (0.012 mole) in acetic acid is stirred at room temperature for 16 hours. The solvent is removed to give 3-bromo-3-(4-fluorobenzoyl)propionic acid.

The preceding compound (1.38 g.; 5 mmole), 0.735 g. (5 mmole) of methyl L-thiazolidine-4-carboxylate and 1.24 g. (5 mmole) of ethyl 1,2-dihydro-2-ethoxy-1-quinolinecarboxylate (EEDQ) in 50 ml. of dichloromethane is stirred at room temperature for 18 hours. The mixture is washed with cold dilute hydrochloric acid, dilute sodium bicarbonate solution and dried over sodium sulfate. The solvent is removed in vacuo to give 2.12 g. of a yellow oil. Chromatography on a silica gel column with dichloromethane as solvent gives methyl [4R]-3-(3-bromo-3-benzoylpropionyl)-4-thiazolidinecarboxylate as an oil.

The preceding compound (0.49 g.) is stirred with sodium thioacetate (2.4 mmole) in 25 ml. of ethanol for 5 minutes. To the mixture is added 1.5 ml. of acetic acid. The solvent is removed and the residue is chromatographed on a silica gel column with dichloromethane as eluent. The product is further purified on a thick silica gel plate with acetone-hexane (1:2) as solvent to give 0.1 g. of the product of the Example as an oil.

EXAMPLE 18

Methyl [4R]-3-(2-acetylthio-3-benzoylpropionyl)-2-(m-trifluoromethylphenyl)-4-thiazolidinecarboxylate A mixture of 19.0 g. (68.5 mmole) of [4R]-2-(m-trifluoromethylphenyl)-4-thiazolidinecarboxylic acid and 400 ml. of methanol saturated with anhydrous hydrogen chloride gas is refluxed for 1.5 hours. The solvent is removed in vacuo and the residue is dissolved in dichloromethane and washed with cold sodium bicarbonate solution. The organic layer is dried over sodium sulfate and concentrated in vacuo to give 18.6 g. of a yellow oil. The oil in dichloromethane is passed through a silica gel column to give 18 g. of methyl 2-(m-trifluoromethylphenyl)-4-thiazolidinecarboxylate as a pale yellow oil [one spot on thin layer chromatography; silica gel; solvent acetone:hexane (1:2)].

A mixture of the preceding compound (2.91 g.; 0.01 mole), 1.76 g. (0.01 mole) of 3-benzoylacrylic acid and 2.47 g. (0.01 mole) of ethyl 1,2-dihydro-2-ethoxy-1-quinolinecarboxylate (EEDQ) in 75 ml. of dichloromethane is stirred at room temperature for 5 days. The mixture is washed with cold dilute hydrochloric acid and dried over sodium sulfate. The solvent is removed in vacuo. The residue is dissolved in dichloromethane and passed through a column of silica gel to give 4.7 g. of yellow oil. An 8.6 g. sample of the yellow oil is chromatographed on a Waters Prep 500 HPLC apparatus with ethyl acetate-hexane as solvent to give 6.8 g. of methyl [4R]-3-(3-benzoylacrylolyl)-2-(m-trifluoromethylphenyl)-4-thiazolidinecarboxylate (yellow oil).

A mixture of the preceding compound (0.5 g; 1 mmole) and 0.15 g. (2 mmole) of thiolacetic acid in 10 ml. of dichloromethane is stirred for 3 hours, then the solvent is removed. The residual gum is chromatographed on a silica gel column with acetone:hexane (1:2) to give 0.44 g. of the product of the Example as a white glass.

EXAMPLE 19

Methyl [4R]-3-[3-acetylthio-3-(4-bromobenzoyl)propionyl]-4-thiazolidinecarboxylate A mixture of 7.0 g. (0.048 mole) of methyl L-thiazolidine-4-carboxylate, 12.34 g. (0.048 mole) of 3-(4-bromobenzoyl)propionic acid and 11.87 g. (0.048 mole) of ethyl 1,2-dihydro-2-ethoxy-1-quinolinecarboxylate (EEDQ) in 250 ml. of dichloromethane is stirred at room temperature for 18 hours. The mixture is filtered and the filtrate is washed with cold dilute hydrochloric acid and dried over sodium sulfate. The solvent is removed in vacuo to give 21.0 g. of an oil. The oil is purified using a Waters 500 HPLC apparatus (μ-Porasil Column) to give methyl [4R]-3-[3-(4-bromobenzoyl)-propionyl]-4-thiazolidinecarboxylate.

A mixture of the preceding compound, bromine and dichloromethane is stirred for 8 hours. The mixture is washed with water and dried over sodium sulfate. To the mixture is added potassium thioacetate and, after stirring for 6 hours, acetic acid is added and the solvent is removed to give the product of the Example.

EXAMPLE 20

Methyl [4R]-3-(2-acetylthio-3-benzoylpropionyl)-4-thiazolidinecarboxylate

A mixture of 1.76 g. (0.01 mole) of 3-benzoylacrylic acid, 1.47 g. (0.01 mole) of methyl L-thiazolidine-4-carboxylate and 2.47 g. (0.01 mole) of ethyl 1,2-dihydro-2-ethoxy-1-quinolinecarboxylate (EEDQ) in 75 ml. of dichloromethane is stirred at room temperature for 18 hours. The mixture is washed with cold dilute hydrochloric acid, dried over sodium sulfate, then the solvent is removed in vacuo. The residue is dissolved in dichloromethane and thioacetic acid is added. The mixture is stirred for 8 hours and the solvent is removed. The residue is chromatographed over silica gel to give the product of the Example.

EXAMPLE 21

[4R]-3-(3-Acetylthio-3-benzoylpropionyl)-4-thiazolidinecarboxylic acid

A mixture of 2.66 g. (0.02 mole) of L-thiazolidine-4-carboxylic acid and 3.63 g. (0.02 mole) of dicyclohexylamine is warmed on a steam bath. To the mixture is added 100 ml. of acetonitrile:dioxane (1:1) and 5.5 g. (0.02 mole) of 3-benzoylpropionic acid, N-hydroxysuccinimide ester. The mixture is refluxed for 4 hours. The mixture is concentrated in vacuo and the residue is dissolved in dichloromethane. The solution is washed with sodium bisulfate solution and dried over sodium sulfate. The solvent is removed and the residual oil is dissolved in dichloromethane. The dichloromethane is extracted with cold saturated sodium bicarbonate solution and the extract is added dropwise to a cold dilute hydrochloric acid solution. Addition of dichloromethane and ethyl acetate causes a solid to separate. The mixture is filtered to give 1.1 g. of [4R]-3-(3-benzoylpropionyl)-4-thiazolidinecarboxylic acid, m.p. 155°–159° C. Recrystallization from acetone-hexane gives 1.0 g. of cream colored crystals, m.p. 159°–161° C.; $[\alpha]_D^{24} -97° \pm 1$ (c, 1.13 $CH_3OH$).

To 2.0 g. (7.0 mmole) of the preceding compound in 50 ml. of acetic acid is added anhydrous hydrogen bromide gas and 1.12 g. (7.0 mmole) of bromine. The mixture is stirred at room temperature for 18 hours. The mixture is concentrated in vacuo. Ether is added to the residue and the mixture is filtered. The solvent is removed and the residue is dissolved in dichloromethane and extracted with saturated sodium bicarbonate solution. The extract is added dropwise to cold dilute hydrochloric acid. The mixture is extracted with dichloromethane and the extract is dried over sodium sulfate and concentrated in vacuo to give 2.5 g. of [4R]-3-(3-bromo-3-benzoylpropionyl)-4-thiazolidinecarboxylate as a glass; $[\alpha]_D^{23} -82° \pm 1$ (c, 0.965, $CH_3OH$).

The preceding compound 1.1 g. (3 mmole) is added to a mixture of sodium thioacetate [prepared from 3.5 mmole of sodium hydride and 0.27 g. (3.5 mmole) of thiolacetic acid] in 30 ml. of dry acetonitrile. The mixture is stirred for 18 hours and filtered. To the filtrate is added several drops of acetic acid and the solvent is removed in vacuo. The residue is triturated with ether to give the product of the Example as a glass.

EXAMPLE 22

[4R]-3-[3-Acetylthio-3-(4-fluorobenzoyl)propionyl]-4-thiazolidinecarboxylic acid Substituting 3-(4-fluorobenzoyl)propionic acid for 3-benzoylpropionic acid in the procedure of Example 21 gives the product of the Example.

EXAMPLE 23

[4R]-3-[3-Acetylthio-3-(4-methoxy-3-fluorobenzoyl)-propionyl]-4-thiazolidinecarboxylic acid Substituting 3-(4-methoxy-3-fluorobenzoyl)propionic acid for 3-benzoylpropionic acid in the procedure of Example 21 gives the product of the Example.

EXAMPLE 24

[4R]-3-[3-Acetylthio-3-(4-phenyloxybenzyl)propionyl]-4-thiazolidinecarboxylic acid

Substituting 3-(4-phenoxybenzoyl)propionic acid for 3-benzoylpropionic acid in the procedure of Example 21 gives the product of the Example.

EXAMPLE 25

[4R]-3-{3-Acetylthio-3-[4-(4-chlorophenoxy)benzoyl]-propionyl}-4-thiazolidinecarboxylic acid

Substituting 3-[4-(4-chlorophenoxy)benzoyl]propionic acid for 3-benzoylpropionic acid in the procedure of Example 21 gives the product of the Example.

EXAMPLE 26

[4R]-3-[3-Acetylthio-3-(3-chlorobenzoyl)propionyl]-4-thiazolidinecarboxylic acid

Substituting 3-(3-chlorobenzoyl)propionic acid for 3-benzoylpropionic acid in the procedure of Example 21 gives the product of the Example.

EXAMPLE 27

[4R]-3-[3-Acetylthio-3-(3,4-dimethoxybenzoyl)propionyl]-4-thiazolidinecarboxylic acid

Substituting 3-(3,4-dimethoxybenzoyl)propionic acid for 3-benzoylpropionic acid in the procedure of Example 21 gives the product of the Example.

EXAMPLE 28

[4R]-3-[3-Acetylthio-3-(2-naphthoyl)propionyl]-4-thiazolidinecarboxylic acid

Substituting 3-(2-naphthoyl)propionic acid, m.p. 167°-170° C., for 3-benzoylpropionic acid in the procedure of Example 21 gives the product of the Example.

EXAMPLE 29

[4R]-3-[3-Acetylthio-3-(3,4,5-trimethoxybenzoyl)propionyl]-4-thiazolidinecarboxylic acid

Substituting 3-(3,4,5-trimethoxybenzoyl)propionic acid for 3-benzoylpropionic acid in the procedure of Example 21 gives the product of the Example.

EXAMPLE 30

[4R]-3-[3-Acetylthio-3-(4-biphenylylcarbonyl)propionyl]-4-thiazolidinecarboxylic acid

Substituting 3-(4-biphenylylcarbonyl)propionic acid for 3-benzoylpropionic acid in the procedure of Example 21 gives the product of the Example.

EXAMPLE 31

[4R]-3-[3-Acetylthio-3-(4-methoxy-1-naphthoyl)propionyl]-4-thiazolidinecarboxylic acid

Substituting 3-(4-methoxy-1-naphthoyl)propionic acid for 3-benzoylpropionic acid in the procedure of Example 21 gives the product of the Example.

EXAMPLE 32

[4R]-3-[3-Acetylthio-3-(1-naphthoyl)propionyl]-4-thiazolidinecarboxylic acid

Substituting 3-(1-naphthoyl)propionic acid for 3-benzoylpropionic acid in the procedure of Example 21 gives the product of the Example.

EXAMPLE 33

[4R]-3-[3-Acetylthio-3-(5-indanylcarbonyl)propionyl]-4-thiazolidinecarboxylic acid

Substituting 3-(5-indanylcarbonyl)propionic acid for 3-benzoylpropionic acid in the procedure of Example 21 gives the product of the Example.

EXAMPLE 34

**[4R-(4R*,2'S*)]-3-(3-Acetylthio-3-benzoyl-2-methylpropionyl)-4-thiazolidinecarboxylic acid**

A mixture of 2.0 g. (0.015 mole) of L-thiazolidine-4-carboxylic acid and 2.72 g. (0.015 mole) of dicyclohexylamine is warmed on a steam bath. To the mixture is added 50 ml. of dioxane, 50 ml. of acetonitrile and 4.2 g. (0.015 mole) of 3-benzoyl-2-methylpropionic acid, N-hydroxysuccinimide ester (prepared from 3-benzoyl-2-methylpropionic acid N-hydroxysuccinimide and N,N-dicyclohexylcarbodiimide in tetrahydrofuran). The mixture is refluxed for 48 hours and concentrated in vacuo. The residue is dissolved in dichloromethane, washed with sodium bisulfate and extracted with saturated sodium bicarbonate. The basic extract is added to dilute hydrochloric acid and extracted with dichloromethane. The organic layer is dried over sodium sulfate and concentrated to an oil. The oil is crystallized from acetone-hexane to give [4R-(4R*,2'R*)]-3-(3-benzoyl-2-methylpropionyl)-4-thiazolidinecarboxylic acid as off-white crystals, m.p. 182°-183° C.; $[\alpha]_D^{23} -63° \pm 4$ (c, 0.24, $CH_3OH$).

The preceding compound is converted to the desired product as described in the procedure of Example 1.

EXAMPLE 35

**[4R-(4R*,2'S*)]-3-[3-Acetylthio-3-(4-chlorobenzoyl)-2-methylpropionyl]-4-thiazolidinecarboxylic acid**

Substituting 3-(4-chlorobenzoyl)-2-methylpropionic acid for 3-benzoyl-2-methylpropionic acid in the procedure of Example 34 gives the product of the Example.

EXAMPLE 36

**[4R-(4R*,2'S)]-3-[3-Acetylthio-3-(3-fluorobenzoyl)-2-methylpropionyl]-4-thiazolidinecarboxylic acid**

Substituting 3-(3-fluorobenzoyl)-2-methylpropionic acid for 3-benzoyl-2-methylpropionic acid in the procedure of Example 34 gives the product of the Example.

EXAMPLE 37

**[4R-(4R*,2'S*)]-3-[3-Acetylthio-3-(5-indanylcarbonyl)-2-methylpropionyl]-4-thiazolidinecarboxylic acid**

Substituting 3-(5-indanylcarbonyl)-2-methylpropionic acid for 3-benzoyl-2-methylpropionic acid in the procedure of Example 34 gives the product of the Example.

EXAMPLE 38

[4R]-3-(2-Acetylthio-3-benzoylpropionyl)-4-thiazolidinecarboxylic acid, 2,4,6-trimethylbenzyl ester

To a solution of 6.66 g. (0.050 mole) of L-thiazolidine-4-carboxylic acid in 80 ml. of water, containing 8.4 g. (0.10 mole) of sodium bicarbonate is added, in portions over 15 minutes, a solution of 11.8 g. (0.054 mole) of di-tert-butyldicarbonate in 80 ml. of dioxane. The mixture is stirred at room temperature for 18 hours, chilled and acidified with 10 ml. of concentrated hydrochloric acid in 50 ml. of water. The mixture is extracted with ethyl acetate and the organic layer is separated, dried over sodium sulfate and concentrated in vacuo to give 13.2 g. of an oil. The oil is crystallized from hexane to give 11.5 g. of white crystals, m.p. 124°–127° C.

A mixture of the preceding compound (10.0 g; 0.043 mole), 4.35 g. (0.043 mole) of triethylamine and 7.23 g. (0.043 mole) of 2,4,6-trimethylbenzyl chloride in 50 ml. of dry N,N-dimethylformamide is stirred at room temperature for two weeks. The mixture is poured into water and extracted with ethyl acetate. The organic layer is dried over sodium sulfate and concentrated in vacuo to give 18.8 g. of a yellow oil. The oil is dissolved in dichloromethane and passed through a short column of hydrous magnesium silicate. Concentration of the filtrate gives an oil which crystallizes from hexane to give [4R]-3,4-thiazolidinedicarboxylic acid, 3-tert-butyl ester, 4-(2,4,6-trimethylbenzyl)ester as white crystals, m.p. 60°–62° C.

A 2.0 g. sample of the preceding compound is stirred with 25 ml. of 90% formic acid at room temperature for 2 hours. The mixture is concentrated in vacuo and the residue is dissolved in ethyl acetate. The solution is washed with sodium bicarbonate solution, dried over sodium sulfate and concentrated to an oil. Hexane is added to the oil to give L-thiazolidine-4-carboxylic acid 2,4,6-trimethylbenzyl ester as white crystals, m.p. 90°–91° C.

A mixture of the preceding compound (3.8 g.; 14.3 mmole), 2.52 g. (14.3 mmole) of 3-benzoylacrylic acid, 3.54 g. (14.3 mmole) of ethyl 1,2-dihydro-2-ethoxy-1-quinolinecarboxylate (EEDQ) and 100 ml. of dichloromethane is stirred at room temperature for 18 hours under argon. The mixture is washed with dilute hydrochloric acid, dried over sodium sulfate and the solvent removed. The residual oil is triturated with hexane to give 4.8 g. of crystals, m.p. 129°–131° C. Recrystallization from dichloromethane-hexane gives 4.4 g. of cream colored crystals, m.p. 130°–132° C.

The preceding compound (1.0 g.; 2.4 mmole) is stirred with 0.37 g. (4.8 mmole) of thiolacetic acid in 30 ml. of dichloromethane for 48 hours. The solvent is removed and the residue in dichloromethane is passed through a short column of silica gel. The filtrate is concentrated to give 0.5 g. of the product of the Example as a cream colored glass.

EXAMPLE 39

[4R]-3-[2-Acetylthio-3-(4-chlorobenzoyl)propionyl]-4-thiazolidinecarboxylic acid, 2,4,6-trimethylbenzyl ester A mixture of 1.0 g. (4 mmole) of L-thiazolidine-4-carboxylic acid, 2,4,6-trimethylbenzyl ester, 4 mmole of 3-(p-chlorobenzoyl)acrylic acid, 0.99 g. (4 mmole) of ethyl 1,2-dihydro-2-ethoxy-1-quinolinecarboxylate (EEDQ) and 50 ml. of dichloromethane is stirred at room temperature for 48 hours. The mixture is washed with cold dilute hydrochloric acid, dried over sodium sulfate and the solvent is removed. The residue is dissolved in dichloromethane and 8 mmole of thiolacetic acid is added. The mixture is stirred at room temperature for 24 hours, then the solvent is removed to give the product of the Example.

EXAMPLE 40

[4R]-3-(2-Acetylthio-3-benzoylpropionyl)-4-thiazolidinecarboxylic acid

A mixture of 1.0 g. of [4R]-3-(2-acetylthio-3-benzoylpropionyl)-4-thiazolidinecarboxylic acid, 2,4,6-trimethylbenzyl ester, 10 ml. of acetic acid and 10 ml. of acetic acid saturated with hydrogen bromide gas is stirred at room temperature for 10 hours. The solvent is removed and the residue is chromatographed on a column of silica gel to give the product of the Example as a glass.

EXAMPLE 41

[4R]-3-[3-Acetylthio-3-(4-fluorobenzoyl)propionyl]-4-thiazolidinecarboxylic acid, 2,4,6-trimethylbenzyl ester A mixture of 2.65 g. of L-thiazolidine-4-carboxylic acid, 2,4,6-trimethylbenzyl ester, 2.75 g. of 3-bromo-3-(4-fluorobenzoyl)propionic acid, 2.47 g. of ethyl 1,2-dihydro-2-ethoxy-1-quinolinecarboxylate (EEDQ) and 200 ml. of dichloromethane is stirred at room temperature for 18 hours. The mixture is washed with cold dilute hydrochloric acid, dried over sodium sulfate and the solvent is removed to give 6.2 g. of a yellow oil. Column chromatography on silica gel with acetone hexane as eluent gives [4R]-3-[3-bromo-3-(4-fluorobenzoyl)propionyl]-4-thiazolidinecarboxylic acid, 2,4,6-trimethylbenzyl ester.

A mixture of the preceding compound (0.522 g.; 1.0 mmole), 2.0 mmole of sodium thioacetate, 1.0 mmole of thiolacetic acid and 5 ml. of ethanol is stirred for 15 minutes. To the mixture is added one ml. of acetic acid and water is added. The mixture is extracted with dichloromethane. The organic layer is dried over sodium sulfate and concentrated to give 0.6 g. of yellow glass. Purification on a thick layer chromatographic plate with acetone:hexane (1:3) gives 0.45 g. of the product of the Example as a yellow glass.

EXAMPLE 42

[4R]-3-(3-Acetylthio-3-benzoyl-2-methylpropionyl)-4-thiazolidinecarboxylic acid, 2,4,6-trimethylbenzyl ester A mixture of 0.265 g. of L-thiazolidine-4-carboxylic acid, 2,4,6-trimethylbenzyl ester, 0.271 g. of 3-bromo-3-benzoyl-2-methylpropionic acid and 0.247 g. of ethyl 1,2-dihydro-2-ethoxy-1-quinolinecarboxylate (EEDQ) in 25 ml. of dichloromethane is stirred under argon at room temperature for 4 days. The mixture is washed with cold dilute hydrochloric acid, dried over sodium sulfate and the solvent is removed in vacuo. The residue is dissolved in dichloromethane:acetonitrile (1:1) and potassium thioacetate is added. The mixture is stirred for 5 hours, acetic acid is added and the solvent is removed in vacuo to give the product of the Example as a mixture of diastereomers.

EXAMPLE 43

[4R]-3-(2-Acetylthio-3-benzoylpropionyl)-4-thiazolidinecarboxylic acid

To a mixture of 1.0 g. of [4R]-3-(3-benzoylacryloyl)-4-thiazolidinecarboxylic acid, 2,4,6-trimethylbenzyl ester in 10 ml. of acetic acid is added 10 ml. of acetic acid saturated with anhydrous hydrogen bromide gas. The mixture is stirred at room temperature for 18 hours and the solvent is removed. The residue is partitioned between ether and sodium bicarbonate solution. The basic aqueous layer is acidified with aqueous hydrochloric acid and extracted with ether. The ether extract is dried over sodium sulfate and the solvent is removed to give 0.4 g. of yellow oil. Crystallization from acetone-hexane gives 0.35 g. of [4R]-3-(3-benzoylacryloyl)-4-thiazolidinecarboxylic acid as off-white crystals, m.p. 146°–148° C.

acid in dichloromethane to give the product of the Example as a yellow glass.

EXAMPLE 44

[4R]-3-(3-Benzoylthio-3-benzoylpropionyl)-4-thiazolidinecarboxylic acid

A mixture of 2.66 g. (0.02 mole) of L-thiazolidine-4-carboxylic acid, 1.36 g. (0.02 mole) of imidazole and 10 ml. of water is warmed on a steam bath. The solvent is removed in vacuo. The residue is stripped several times with toluene. To the residue is added 2.75 g. (0.010 mole) of 3-benzoylpropionic acid, N-hydroxysuccinimide ester and 100 ml. of acetonitrile. The mixture is refluxed for 4 hours and the solvent is removed in vacuo. The residue is partitioned between dilute hydrochloric acid and dichloromethane. The organic layer is dried over sodium sulfate and concentrated in vacuo. The residue in dichloromethane-hexane gives crystals. Recrystallization from dichloromethane-ether-hexane gives off-white crystals, m.p.. 155°–158° C.

The preceding compound is reacted with bromine and then with sodium thiobenzoate as in the procedure of Example 21 to give the product of the Example as a pale yellow glass.

EXAMPLE 45

[4R]-3-(2-Benzoylthio-3-benzoylpropionyl)-4-thiazolidinecarboxylic acid

To a mixture of 2.0 g. of [4R]-3-(3-benzoylacryloyl)-4-thiazolidinecarboxylic acid, 2,4,6-trimethylbenzyl ester in 20 ml. of acetic acid is added 20 ml. of acetic acid saturated with anhydrous hydrogen bromide gas. The mixture is stirred at room temperature for 18 hours and the solvent is removed in vacuo. The residue is partitioned between ether and dilute sodium bicarbonate solution. The basic aqueous layer is added dropwise to dilute hydrochloric acid. The mixture is extracted with ether and the organic layer is dried over sodium sulfate. The solvent is removed to give 2.8 g. of oily solid. Crystallization from acetone-hexane gives 1.0 g. of off-white crystals, m.p. 146°–148° C.

The preceding compound is stirred with thiobenzoic acid in dichloromethane to give the product of the Example as a glass.

EXAMPLE 46

[4R]-3-(3-Acetylthio-3-benzoylpropionyl)-2,2-dimethyl-4-thiazolidinecarboxylic acid A mixture of 20.0 g. (0.17 mole) of L-cysteine and 500 ml. of acetone is refluxed for 48 hours. The mixture is filtered through a thin pad of diatomaceous earth and the filtrate is concentrated to one-half volume. Chilling and filtering gives 20.5 g. of white crystals, m.p. 133°–139° C. Recrystallization from acetone gives 16.0 g. of L-2,2-dimethylthiazolidine-4-carboxylic acid as white crystals, m.p. 139°–143° C.

The preceding compound (1.61 g.; 0.01 mole) and 1.81 g. of N,N-dicyclohexylamine is warmed on a steam bath then 50 ml. of dioxane and 50 ml. of acetonitrile are added. To the warmed mixture is added 2.8 g. (0.01 mole) of 3-benzoylpropionic acid, N-hydroxysuccinimide ester. The mixture is refluxed for 18 hours and concentrated in vacuo. The residue is dissolved in dichloromethane, washed with sodium bisulfate and extracted with sodium bicarbonate solution. The basic solution is added to dilute hydrochloric acid and extracted with ethyl acetate. The organic layer is dried over sodium sulfate and the solvent removed to give [4R]-3-(3-benzoylpropionyl)-2,2-dimethyl-4-thiazolidinecarboxylic acid.

The preceding compound is reacted with bromine, then with potassium thioacetate as in the procedure of Example 1 to give the product of the Example as a glass.

EXAMPLE 47

[4R]-3-(3-Acetylthio-3-benzoyl-2-methylpropionyl)-2,2-dimethyl-4-thiazolidinecarboxylic acid, 2,4,6-trimethylbenzyl ester To a solution of L-2,2-dimethylthiazolidine-4-carboxylic acid (15.4 g.; 0.096 mole) in 160 ml. of water containing 16.8 g. (0.2 mole) of sodium bicarbonate is added dropwise 21.8 g. (0.10 mole) of di-tert-butyldicarbonate in 160 ml. of dioxane over a 0.5 hour period. The mixture is stirred at room temperature for 18 hours, chilled, and 20 ml. of concentrated hydrochloric acid in 100 ml. of water is added. The mixture is extracted with ethyl acetate and the organic layer is dried and the solvent is removed to give 18.3 g. of [4R]-2,2-dimethylthiazolidine-3,4-dicarboxylic acid, 3-tert-butyl ester as an oil.

To a mixture of 16.2 g. (0.062 mole) of the preceding compound and 6.3 g. (0.062 mole) of triethylamine in 150 ml. of dry N,N-dimethylformamide is added 10.5 g. (0.062 mole) of 2,4,6-trimethylbenzyl chloride. The mixture is stirred for 16 hours at room temperature under argon then is poured into one liter of water. The mixture is extracted with ethyl acetate and the extract is washed with water and dried over sodium sulfate. The solvent is removed to give 23.6 g. of oil which is crystallized from hexane to give crystals, m.p. 58°–60° C.

A mixture of the preceding compound (10.0 g.) and 10.0 g. of p-toluenesulfonic acid in 60 ml. of acetonitrile is stirred at room temperature for 5 hours. The mixture is concentrated in vacuo and the residue is partitioned between dichloromethane and sodium bicarbonate solution. The organic layer is dried over sodium sulfate and concentrated in vacuo to give L-2,2-dimethylthiazolidine-4-carboxylic acid, 2,4,6-trimethylbenzyl ester.

Substitution of the preceding compound for L-thiazolidine-4-carboxylic acid in the procedure of Example 1 gives the product of the Example as a mixture of diastereomers.

EXAMPLE 48

[4R]-3-(3-Acetyl-3-benzoyl-2-methylpropionyl)-2,2-dimethyl-4-thiazolidinecarboxylic acid A mixture of 8.39 g. (0.052 mole) of L-2,2-dimethylthiazolidine-4-carboxylic acid and 5.26 g. of triethylamine is heated on a steam bath. To the mixture is added 0.052 mole of a mixture of 3-methyl-5-phenyl-2(3H)-furanone and 3-methyl-5-phenyl-2(5H)-furanone in 150 ml. of dry isopropyl alcohol. The mixture is refluxed for 144 hours and the solvent is removed in vacuo. The residue is partitioned between water and ethyl acetate. The aqueous layer is poured onto crushed ice and acidified with hydrochloric acid. The mixture is extracted with ethyl acetate and the organic layer is dried over sodium sulfate. The solvent is removed to give 4.8 g. of a yellow glass which is a mixture of [4R-(4R*,2'R*)]-3-(3-benzoyl-2-methylpropionyl)-2,2-dimethyl-4-thiazolidinecarboxylic acid and [4R-(4R*,2'S*)]-3-(3-benzoyl-2-methylpropionyl)-2,2-dimethyl-4-thiazolidinecarboxylic acid. The mixture is dissolved in acetic acid containing anhydrous hydrogen bromide gas and to the mixture is added bromine. Removal of the solvent gives a glass which is reacted with potassium thioacetate as in the procedure of Example 1 to give the product of the Example as a mixture of diastereomers.

EXAMPLE 49

[4R-(4R*,2'S*)]-3-(3-Acetylthio-3-benzoyl-2-methylpropionyl)-2-(m-trifluoromethylphenyl)-4-thiazolidinecarboxylic acid A mixture of 14.4 g. (0.052 mole) of [4R]-2-(m-trifluoromethylphenyl)-4-thiazolidinecarboxylic acid and 5.26 g. (0.052 mole) of triethylamine is refluxed for 15 minutes. To the mixture is added 0.052 mole of 3-methyl-5-phenyl-2(3H)-furanone in 150 ml. of dry isopropyl alcohol. The mixture is refluxed for 125 hours, then the solvent is removed. The residue is partitioned between ethyl acetate and water. The aqueous layer is acidified with dilute hydrochloric acid and is extracted with ethyl acetate. The organic layer is dried over sodium sulfate and concentrated to give 7.0 g. of an oil. The oil is dissolved in ether (400 ml.) and hexane is added until the solution is turbid. After standing, there is obtained 4.5 g. of white crystals, m.p. 163°–168° C. Recrystallization from ether-hexane gives 3.2 g. of [4R-(4R*,2'R*)]-3-(3-benzoyl-2-methylpropionyl)-2-(m-trifluoromethylphenyl)-4-thiazolidinecarboxylic acid as off-white crystals, m.p. 175°–179° C.

Substituting the preceding compound for [4R-(4R*,2'R*)]-3-(3-benzoyl-2-methylpropionyl)-4-thiazolidinecarboxylic acid in the procedure of Example 1 gives the product of the Example.

EXAMPLE 50

[4R]-3-[2-Acetylthio-3-(3-fluorobenzoyl)propionyl]-4-thiazolidinecarboxylic acid Substitution of [4R]-3-[3-(3-fluorobenzoyl)acryloyl]-4-thiazolidinecarboxylic acid, 2,4,6-trimethylbenzyl ester for [4R]-3-(3-benzoylacryloyl)-4-thiazolidinecarboxylic acid, 2,4,6-trimethylbenzyl ester in Example 43 gives the product of the Example as a glass.

EXAMPLE 51

Methyl [4R]-3-[2-acetylthio-3-(2-naphthoyl)propionyl]-4-thiazolidinecarboxylate

Substitution of 3-(2-naphthoyl)acrylic acid for 3-benzoylacryllic acid in Example 20 gives the product of the Example as a glass.

EXAMPLE 52

Methyl [4R]-3-[2-acetylthio-3-(4-methoxybenzoyl)propionyl]-4-thiazolidinecarboxylate Substitution of 3-(4-methoxybenzoyl)acrylic acid for 3-benzoylacrylic acid in Example 20 gives the product of the Example.

EXAMPLE 53

Methyl [4R]-3-[2-acetylthio-3-(3,4-dichlorobenzoyl)propionyl]-4-thiazolidinecarboxylate Substitution of 3-(3,4-dichlorobenzoyl)acrylic acid for 3-benzoylacrylic acid in Example 20 gives the product of the Example.

EXAMPLE 54

Ethyl [4R]-3-[2-acetylthio-3-(4-tert-butylbenzoyl)propionyl]-4-thiazolidinecarboxylate Substitution of 3-(4-tert-butylbenzoyl)acrylic acid for 3-benzoylacrylic acid and ethyl L-thiazolidinecarboxylate for methyl L-thiazolidinecarboxylate in Example 20 gives the product of the Example.

EXAMPLE 55

Methyl [4R]-3-[2-acetylthio-3-(4-cyanobenzoyl)propionyl]-4-thiazolidinecarboxylate Substitution of 3-(4-cyanobenzoyl)acrylic acid for 3-benzoylacrylic acid in Example 20 gives the product of the Example.

EXAMPLE 56

Methyl [4R]-3-[2-acetylthio-3-(3,4,5-trimethoxybenzoyl)propionyl]-4-thiazolidinecarboxylate Substitution of 3-(3,4,5-trimethoxybenzoyl)acrylic acid for 3-benzoylacrylic acid in Example 20 gives the product of the Example.

EXAMPLE 57

[4R]-3-[3-Acetylthio-3-(3-fluorobenzoyl)-2-methylpropionyl]-2,2-dimethyl-4-thiazolidinecarboxylic acid Substitution of 3-methyl-5-(3-fluorophenyl)-2(3H)-furanone and 3-methyl-5-(3-fluorophenyl)-2(5H)-furanone for 3-methyl-5-phenyl-2(3H)-furanone and 3-methyl-5-phenyl-2(5H)-furanone in Example 48 gives the product of the Example.

EXAMPLE 58

[4R]-3-[3-Acetylthio-3-(3,4,5-trimethoxybenzoyl)propionyl]-4-thiazolidinecarboxylic acid A mixture of 38.1 g. (0.2 mole) of [4R]-3,4-thiazolidinedcarboxylic acid, 3-tert-butyl ester, 4-(2,4,6-trimethylbenzyl ester, 47.6 g. (0.25 mole) of p-toluenesulfonic acid and 250 ml. of acetonitrile is stirred at room temperature for 5 hours. The solvent is removed in vacuo and the residue is dissolved in dichloromethane. Water is added and to the chilled mixture is added portionwise solid sodium bicarbonate until the aqueous layer is alkaline. The organic layer is separated, dried over sodium sulfate and concentrated to a white solid. The solid is heated with boiling hexane, filtered from some insoluble material and the filtrate is chilled. Filtration gives 24.8 g. of L-4-thiazolidinecarboxylic acid, 2,4,6-trimethylbenzyl ester as white crystals, m.p. 83°–88° C. Recrystallization from 450 ml. of ethylacetate:hexane (1:2) gives 15 g. of white crystals, m.p. 96°–98° C.

A mixture of the preceding compound, ethyl 1,2-dihydro-2-ethoxy-1-quinolinecarboxylate (EEDQ) and 3-(3,4,5-trimethoxybenzoyl)propionic acid in dichloromethane is stirred at room temperature for 24 hours. The mixture is washed with dilute hydrochloric acid, dried over sodium sulfate and the solvent removed to give [4R]-3-[3-(3,4,5-trimethoxybenzoyl)propionyl]-4-thiazolidinecarboxylic acid, 2,4,6-trimethylbenzyl ester.

The preceding compound is stirred with a solution of anhydrous hydrogen bromide in acetic acid to give [4R]-3-[3-(3,4,5-trimethoxybenzoyl)propionyl]-4- thiazolidinecarboxylic acid. The preceding compound is reacted with bromine in acetic acid and the brominated derivative is reacted with potassium thioacetate as described in the procedure of Example 1 to give the product of the Example.

EXAMPLE 59

[4R]-3-[3-Acetylthio-3-(1-naphthoyl)propionyl]-2-(m-trifluoromethylphenyl)-4-thiazolidinecarboxylic acid A mixture of 55.45 g. (0.20 mole) of [4R]-2-(m-trifluoromethylphenyl)-4-thiazolidinecarboxylic acid, 33.6 g. (0.40 mole) of sodium bicarbonate and 320 ml. of water is stirred at room temperature for 0.5 hours. To the mixture is added 100 ml. of p-dioxane. To the stirred solution is added dropwise, over a 0.5 hour period, a solution of di-tert-butyldicarbonate in 220 ml. of dioxane. The mixture is stirred at room temperature for 18 hours, chilled and acidified by the dropwise addition of 40 ml. of concentrated hydrochloric in 200 ml. of water. The mixture is extracted with ethyl acetate and the organic layer is dried over sodium sulfate. The solvent is removed to give an oil which is crystallized from n-hexane to give 64.0 g. of [4R]-2-(m-trifluoromethylphenyl)-3,4-thiazolidinecarboxylic acid, 3-tert-butyl ester as white crystals, m.p. 106°–108° C.

To a solution of 61.69 g. (0.16 mole) of the preceding compound and 16.2 g. (0.16 mole) of triethylamine in 300 ml. of dry N,N-dimethylformamide is added 27.57 g. (0.16 mole) of 2,4,6-trimethylbenzyl chloride. The mixture is stirred at room temperature for 18 hours upon argon and poured into a saline solution. The mixture is extracted with ethyl acetate and the organic layer is dried over sodium sulfate and concentrated in vacuo to give a solid. Recrystallization from dichloromethane-hexane gives 34.0 g. of [4R]-2-(m-trifluoromethylphenyl)-3,4-thiazolidinecarboxylic acid, 3-tert-butyl ester, 4-(2,4,6-trimethylbenzyl)ester as white crystals, m.p. 98°–99° C. The preceding compound is stirred with formic acid for 5 hours to give [4R]-2-(m-trifluoromethylphenyl)-4-thiazolidinecarboxylic acid, 2,4,6-trimethylbenzyl ester.

A mixture of the preceding compound (0.01 mole), ethyl 1,2-dihydro-2-ethoxy-1-quinolinecarboxylate (EEDQ) (0.01 mole) and 3-(1-naphthoyl)propionic acid (0.01 mole) in dichloromethane is stirred for 24 hours. The mixture is washed with dilute hydrochloric acid, dried over sodium sulfate and the solvent is removed to give [4R]-3-[3-(1-naphthoyl)propionyl]-2-(m-trifluoromethylphenyl)-4-thiazolidinecarboxylic acid, 2,4,6-trimethylbenzyl ester.

The preceding compound is stirred with a solution of anhydrous hydrogen bromide in acetic acid to give [4R]-3-[3-(1-naphthoyl)propionyl]-2-(m-trifluoromethylphenyl)-4-thiazolidinecarboxylic acid. Reaction of the preceding compound with bromine in acetic acid and reacting the brominated derivative with potassium thioacetate as described in the procedure for Example 1 gives the product of the Example.

EXAMPLE 60

[4R-(4R*,2′S*)]-3-(3-Acetylthio-3-benzoyl-2-methylpropionyl)-2-(p-chlorophenyl)-4-thiazolidinecarboxylic acid Substitution of [4R]-2-(p-chlorophenyl)-4-thiazolidinecarboxylic acid for [4R]-2-(m-trifluoromethylphenyl)-4-thiazolidinecarboxylic acid in Example 49 gives the product of the Example.

EXAMPLE 61

[4R-(4R*,2′S*)]-3-(3-Acetylthio-3-benzoyl-2-methylpropionyl)-2-(m-fluorophenyl)-4-thiazolidinecarboxylic acid Substitution of [4R]-2-(m-fluorophenyl)-4-thiazolidinecarboxylic acid for [4R]-2-(m-trifluoromethylphenyl)-4-thiazolidinecarboxylic acid in Example 49 gives the product of the Example.

EXAMPLE 62

[4R-(4R*,2′S*)]-3-(3-Acetylthio-3-benzoyl-2-methylpropionyl)-2-(p-tolyl)-4-thiazolidinecarboxylic acid Substitution of [4R]-2-(p-tolyl)-4-thiazolidinecarboxylic acid for [4R]-2-(m-trifluoromethylphenyl)-4-thiazolidinecarboxylic acid in Example 49 gives the product of the Example.

EXAMPLE 63

[4R-(4R*,2′S*)]-3-(3-Acetylthio-3-benzoyl-2-methylpropionyl)-2-(p-tert-butylphenyl)-4-thiazolidinecarboxylic acid Substitution of [4R]-2-(p-tert-butylphenyl)-4-thiazolidinecarboxylic acid for [4R]-2-(m-trifluoromethylphenyl)-4-thiazolidinecarboxylic acid in Example 49 gives the product of the Example.

EXAMPLE 64

Methyl [4R]-3-(2-acetylthio-3-benzoylpropionyl)-2,2-dimethyl-4-thiazolidinecarboxylic acid Substitution of [4R]-2,2-dimethyl-4-thiazolidinecarboxylic acid, methyl ester for methyl L-thiazolidine-4-carboxylic acid in Example 20 gives the product of the Example.

We claim:

1. A compound selected from the group consisting of those of the formulae:

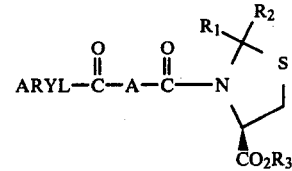

wherein A is

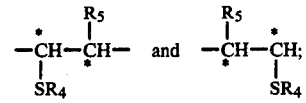

$R_1$ and $R_2$ are selected from the group consisting of hydrogen, lower alkyl ($C_1$–$C_3$), phenyl and mono substituted phenyl, wherein the substituents are chloro, fluoro, trifluoromethyl, lower alkyl ($C_1$–$C_4$), and methoxy, with the proviso that when $R_1$ is phenyl or substituted phenyl, $R_2$ must be hydrogen; $R_3$ is hydrogen, or lower alkyl having from 1–4 carbon atoms; $R_4$ is selected from the group comprising hydrogen, benzoyl and lower alkanoyl ($C_1$–$C_4$); $R_5$ is hydrogen and lower alkyl having from 1–3 carbon atoms; ARYL is selected from the group consisting of 1-naphthyl, 2-naphthyl, 4-chloro-1-naphthyl, 4-methoxy-1-naphthyl, 5,6,7,8-tetrahydro-1-naphthyl, 5,6,7,8-tetrahydro-2-naphthyl, 4-biphenylyl, 5-indanyl, 4-indanyl and moieties of the formula:

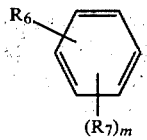

wherein $R_6$ is selected from the group consisting of hydrogen, fluoro, chloro, bromo, trifluoromethyl, cyano, phenoxy, halophenoxy, phenylthio, halophenylthio, alkyl having from 1–4 carbon atoms and alkoxy having from 1–4 carbon atoms; where m is zero, one or two; and the pharmacologically acceptable cationic salts thereof.

2. The compound according to claim 1, [4R-(4R*,2'S*)]-3-(3-acetylthio-3-benzoyl-2-methylpropionyl)-4-thiazolidinecarboxylic acid.

3. The compound according to claim 1, methyl [4R]-3-(2-acetylthio-3-benzoylpropionyl)-2-(m-trifluoromethylphenyl)-4-thiazolidinecarboxylate.

4. The compound according to claim 1, [4R]-3-(2-benzoylthio-3-benzoylpropionyl)-4-thiazolidinecarboxylic acid.

5. The compound according to claim 1, [4R]-3-(2-acetylthio-3-benzoylpropionyl)-4-thiazolidinecarboxylic acid.

6. The compound according to claim 1, [4R]-3-[3-acetylthio-3-(4-fluorobenzoyl)propionyl]-4-thiazolidinecarboxylic acid.

7. The compound according to claim 1, [4R-(4R*,2'S*)]-3-[3-acetylthio-3-(3-fluorobenzoyl)-2-methylpropionyl]-4-thiazolidinecarboxylic acid.

8. The compound according to claim 1, [4R-(4R*,2'S*)]-3-[3-acetylthio-3-(3,4-dichlorobenzoyl)-2-methylpropionyl]-4-thiazolidinecarboxylic acid.

9. The compound according to claim 1, [4R-(4R*,2'S*)]-3-[3-acetylthio-3-(2-naphthoyl)-2-methylpropionyl]-4-thiazolidinecarboxyllic acid.

10. The compound according to claim 1, [4R-(4R*,2'S*)]-3-[3-acetylthio-3-(5-indanylcarbonyl)-2-methylpropionyl]-4-thiazolidinecarboxylic acid.

11. The compound according to claim 1, [4R-(4R*,2'S*)]-3-[3-acetylthio-3-(4-tert-butylbenzoyl)-2-methylpropionyl]-4-thiazolidinecarboxylic acid.

12. The compound according to claim 1, [4R-(4R*,2'S*)]-3-{3-acetylthio-3-[4-(4-chlorophenoxy)benzoyl]-2-methylpropionyl}-4-thiazolidinecarboxylic acid.

13. The compound according to claim 1, [4R-(4R*,2'S*)]-3-(3-acetylthio-3-benzoyl-2-methylpropionyl)-2,2-dimethyl-4-thiazolidinecarboxylic acid.

14. The compound according to claim 1, [4R-(4R*,2'S*)]-3-[3-acetylthio-3-(4-chlorobenzoyl)-2-methylpropionyl)-2,2-dimethyl-4-thiazolidinecarboxylic acid.

15. The compound according to claim 1, [4R]-3-[2-acetylthio-3-(3-fluorobenzoyl)propionyl]-2,2-dimethyl-4-thiazolidinecarboxylic acid.

16. The compound according to claim 1, [4R-(4R*,2'S*)]-3-[3-acetylthio-3-(benzoyl)-2-methylpropionyl]-2-phenyl-4-thiazolidinecarboxylic acid.

17. The compound according to claim 1, [4R-(4R*,2'S*)]-3-[3-acetylthio-3-(1-naphthoyl)-2-methylpropionyl]-2-phenyl-4-thiazolidinecarboxylic acid.

18. The compound according to claim 1, [4R-(4R*,2'R*)]-3-(3-acetylthio-3-benzoyl-2-methylpropionyl)-4-thiazolidinecarboxylic acid.

19. The compound according to claim 1, [4R-(4R*,2'S*)]-3-(3-acetylthio-3-benzoyl-2-methylpropionyl)-2-methyl-4-thiazolidinecarboxylic acid.

20. The compound according to claim 1, [4R-(4R*,2'S*)]-3-(3-acetylthio-3-benzoyl-2-methylpropionyl)-2-phenyl-4-thiazolidinecarboxylic acid.

* * * * *